US012285202B2

(12) United States Patent
Huber et al.

(10) Patent No.: US 12,285,202 B2
(45) Date of Patent: Apr. 29, 2025

(54) DEVICE AND METHOD FOR TISSUE IDENTIFICATION

(71) Applicant: Aesculap AG, Tuttlingen (DE)

(72) Inventors: Christian Huber, Muehlheim (DE); Dieter Weisshaupt, Immendingen (DE); Christoph Rothweiler, Donaueschingen (DE); Detlef Russ, Renningen (DE); Oliver Fugger, Ulm (DE); Raimund Hibst, Erbach (DE); Alwin Kienle, Blaustein (DE); Florian Foschum, Neu-Ulm (DE)

(73) Assignee: Aesculap AG, Tuttlingen (DE)

( * ) Notice: Subject to any disclaimer, the term of this patent is extended or adjusted under 35 U.S.C. 154(b) by 616 days.

(21) Appl. No.: 17/633,025

(22) PCT Filed: Aug. 5, 2020

(86) PCT No.: PCT/EP2020/072028
§ 371 (c)(1),
(2) Date: Feb. 7, 2022

(87) PCT Pub. No.: WO2021/023781
PCT Pub. Date: Feb. 11, 2021

(65) Prior Publication Data
US 2022/0287760 A1 Sep. 15, 2022

(30) Foreign Application Priority Data
Aug. 7, 2019 (DE) ...................... 10 2019 121 365.7

(51) Int. Cl.
*A61B 18/14* (2006.01)
*A61B 18/00* (2006.01)
(52) U.S. Cl.
CPC .............................. *A61B 18/1445* (2013.01); *A61B 2018/00589* (2013.01); *A61B 2018/0063* (2013.01);
(Continued)

(58) Field of Classification Search
CPC .... A61B 118/1445; A61B 2018/00589; A61B 2018/0063; A61B 2018/00666;
(Continued)

(56) References Cited

U.S. PATENT DOCUMENTS 5,725,480 A 3/1998 Oosta et al.
5,743,903 A 4/1998 Stern et al.
(Continued)

FOREIGN PATENT DOCUMENTS

CN 110074856 A 8/2019
DE 69523517 5/2002
(Continued)

OTHER PUBLICATIONS

Communication pursuant to Article 94(3) EPC received in European Application No. 20 753 714.3 dated Feb. 22, 2024, with translation, 13 pages.
(Continued)

Primary Examiner — Linda C Dvorak
Assistant Examiner — Abigail Bock
(74) Attorney, Agent, or Firm — Christopher A. Rothe; CM Law

(57) ABSTRACT

A method for measuring temperature includes emitting light with an illumination spectrum into a tissue with at least one illumination, receiving the remission of light with a remission spectrum from the tissue using at least one detector, converting the remission spectrum into a detector signal, sending the detector signal to a calculating unit, calculating a first theoretical remission spectrum based on a solution for describing the propagation of light in the tissue with the calculating unit, assuming estimated volume fractions of the individual tissue components, adapting the theoretical remission spectrum to the measured remission spectrum, and calculating at least one volume fraction of a tissue
(Continued)

component from the remissions spectrum using a minimization algorithm, which is used by the calculating unit to adapt the theoretical remission spectrum to the measured remission spectrum using variations in the volume fractions of the individual tissue components which are present in the tissue.

11 Claims, 6 Drawing Sheets

(52) U.S. Cl.
CPC ............... *A61B 2018/00666* (2013.01); *A61B 2018/00708* (2013.01); *A61B 2018/00791* (2013.01); *A61B 2018/00875* (2013.01); *A61B 2018/00904* (2013.01)

(58) Field of Classification Search
CPC ........... A61B 2018/00708; A61B 2018/00791; A61B 2018/00875; A61B 2018/00904
See application file for complete search history.

(56) References Cited

U.S. PATENT DOCUMENTS

| | | | |
|---|---|---|---|
| 9,033,983 | B2 | 5/2015 | Takashino et al. |
| 9,763,642 | B2 | 9/2017 | Harks et al. |
| 2002/0169445 | A1 | 11/2002 | Jain et al. |
| 2006/0111622 | A1 | 5/2006 | Merritt et al. |
| 2012/0296238 | A1 | 11/2012 | Chernov et al. |
| 2013/0204134 | A1 | 8/2013 | Harks et al. |
| 2014/0378797 | A1 | 12/2014 | Hendriks et al. |
| 2016/0346034 | A1 | 12/2016 | Arya et al. |
| 2017/0156797 | A1 | 6/2017 | Hendriks et al. |
| 2019/0231193 | A1 | 8/2019 | Hendon et al. |
| 2021/0196374 | A1 | 7/2021 | Xu et al. |

FOREIGN PATENT DOCUMENTS

| | | |
|---|---|---|
| EP | 0694291 A1 | 1/1996 |
| JP | 2000506048 A | 5/2000 |
| JP | 2012239848 A | 12/2012 |
| JP | 2013544551 A1 | 12/2013 |
| WO | 2009005850 A1 | 1/2009 |
| WO | 2009130752 A1 | 10/2009 |

OTHER PUBLICATIONS

Office Action received in Japanese Application No. 2022-507543 dated Mar. 5, 2024, with translation, 13 pages.
Kelly, et al., "Tissue temperature by near-infrared spectroscopy," Proceeding of Spie, SPIEDigitalLibrary.org/conference-proceedings-of-spie, Optical Tomography, Photon Migration, and Spectroscopy of Tissue and Model Media: Theory, Human Studies, and Instrumentation, May 30, 1995, 12 pages.
Nachabé, et al., "Estimation of lipid and water concentrations in scattering media with diffuse optical spectroscopy from 900 to 1600 nm," Journal of Biomedical Optics 15(3), May/Jun. 2010, 10 pages.
Search Report received in German Application No. 10 2019 121 365.7 dated Jun. 15, 2020, with translation, 9 pages.
Search Report received in International Application No. PCT/EP2020/072028 dated Nov. 5, 2020, with translation, 10 pages.
Written Opinion received in International Application No. PCT/EP2020/072028 dated Nov. 5, 2020, with translation, 24 pages.
Hecht, "The Interpretation of Diffuse Reflectance Spectra," Journal of Research of the National Bureau of Standards—A Physics and Chemistry, vol. 80A, No. 4, Jul.-Aug. 1976, 17 pages.
Naglic et al., "Suitability of diffusion approximation for an inverse analysis of diffuse reflectance spectra from human skin in vivo," OSA Continuum, vol. 2, No. 3, Mar. 15, 2019, 18 pages.

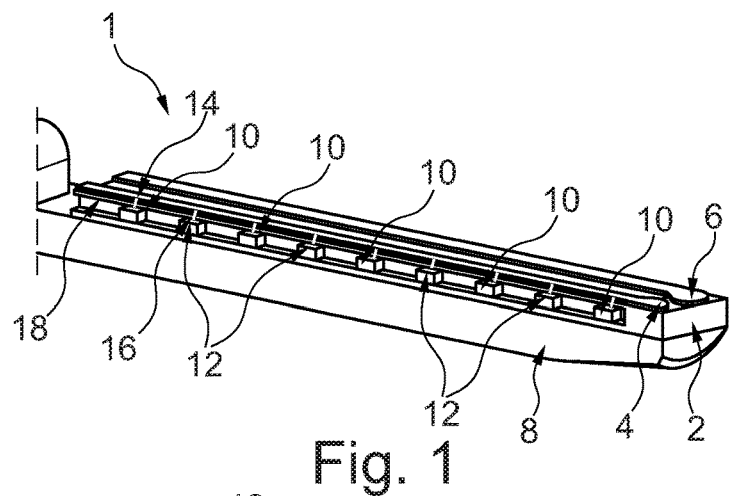
Fig. 1
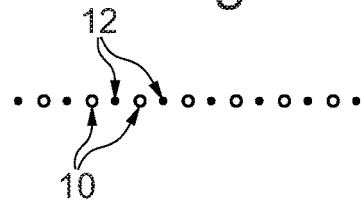
Fig. 2
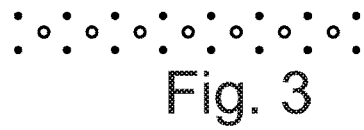
Fig. 3
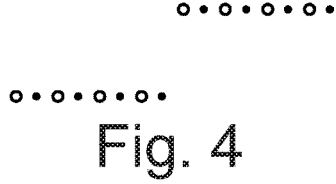
Fig. 4
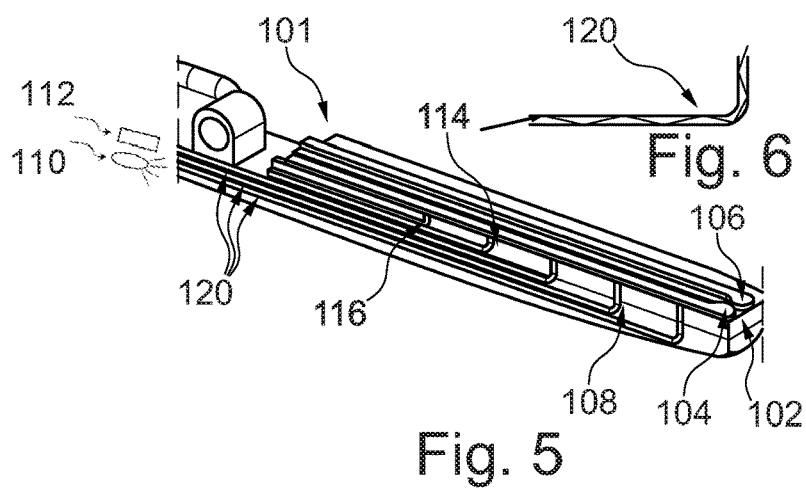
Fig. 5
Fig. 6

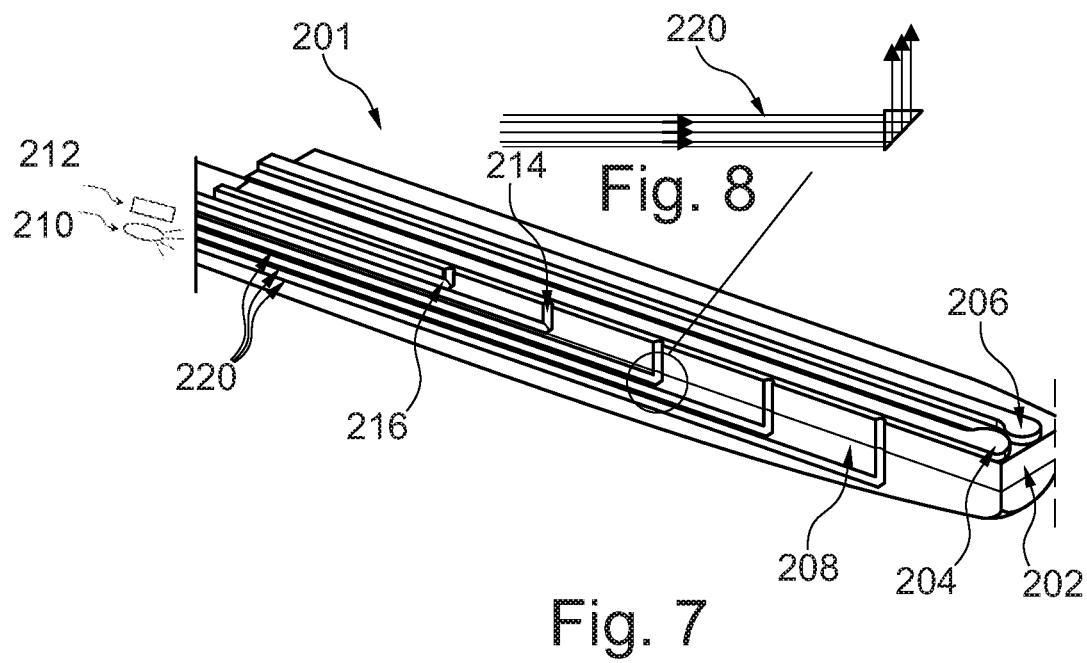
Fig. 8
Fig. 7
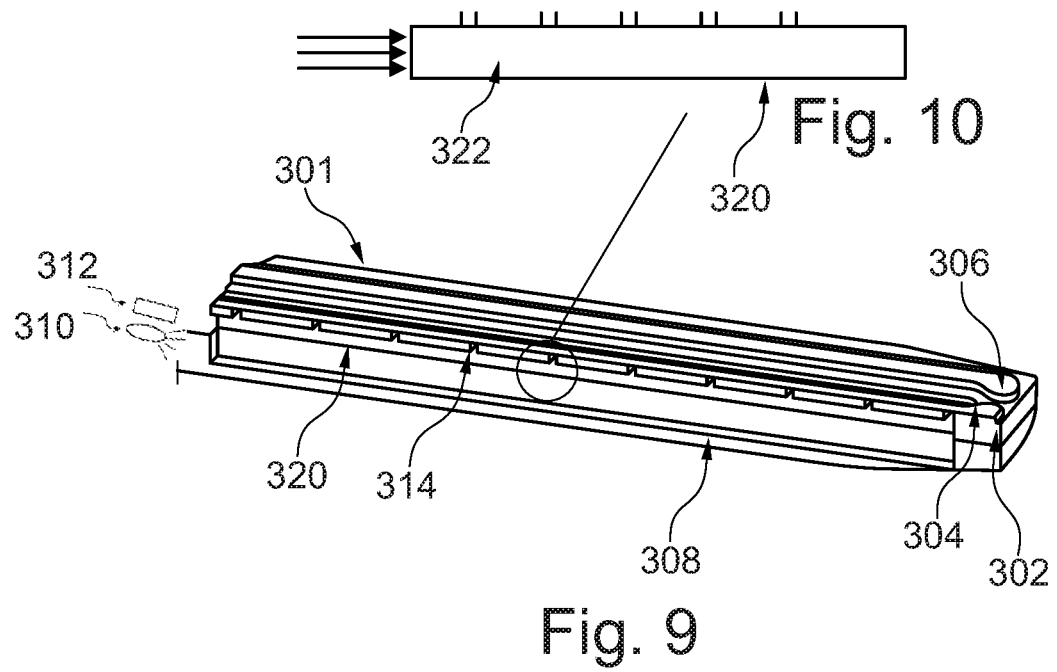
Fig. 10
Fig. 9

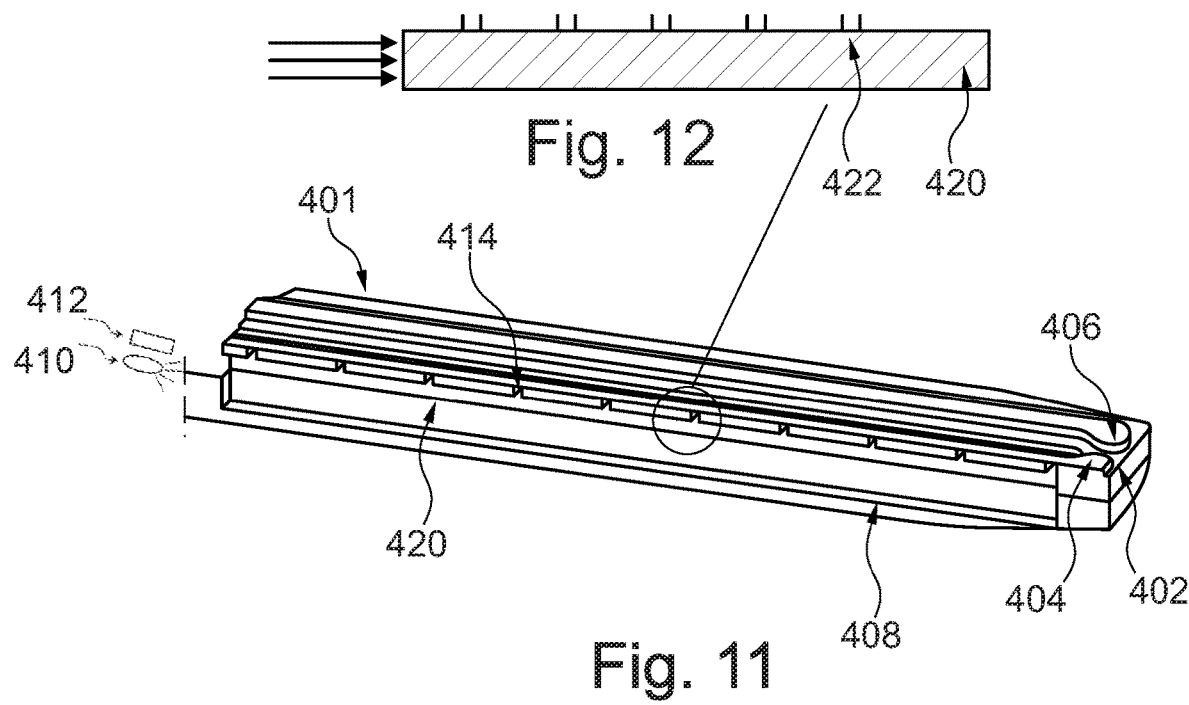
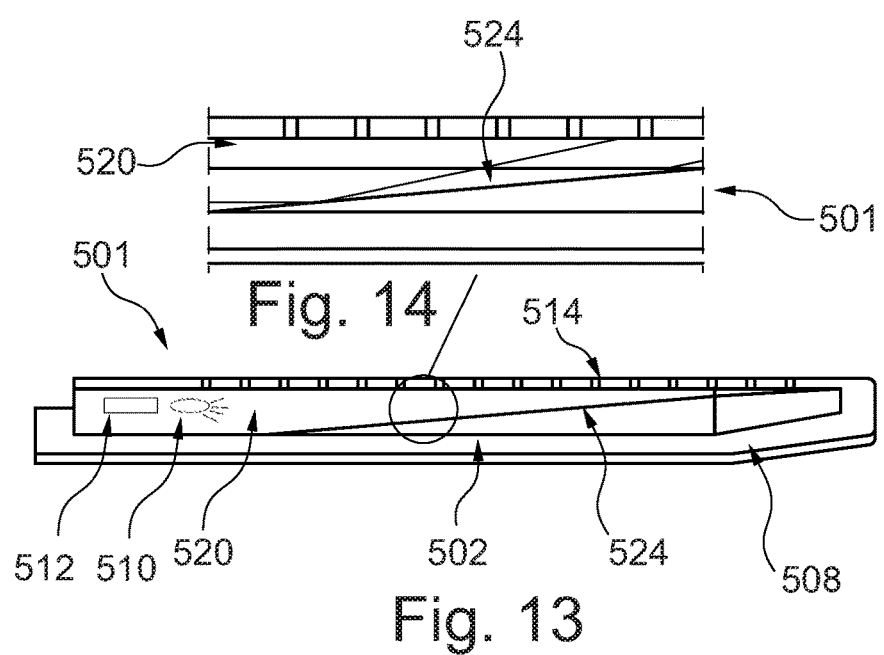

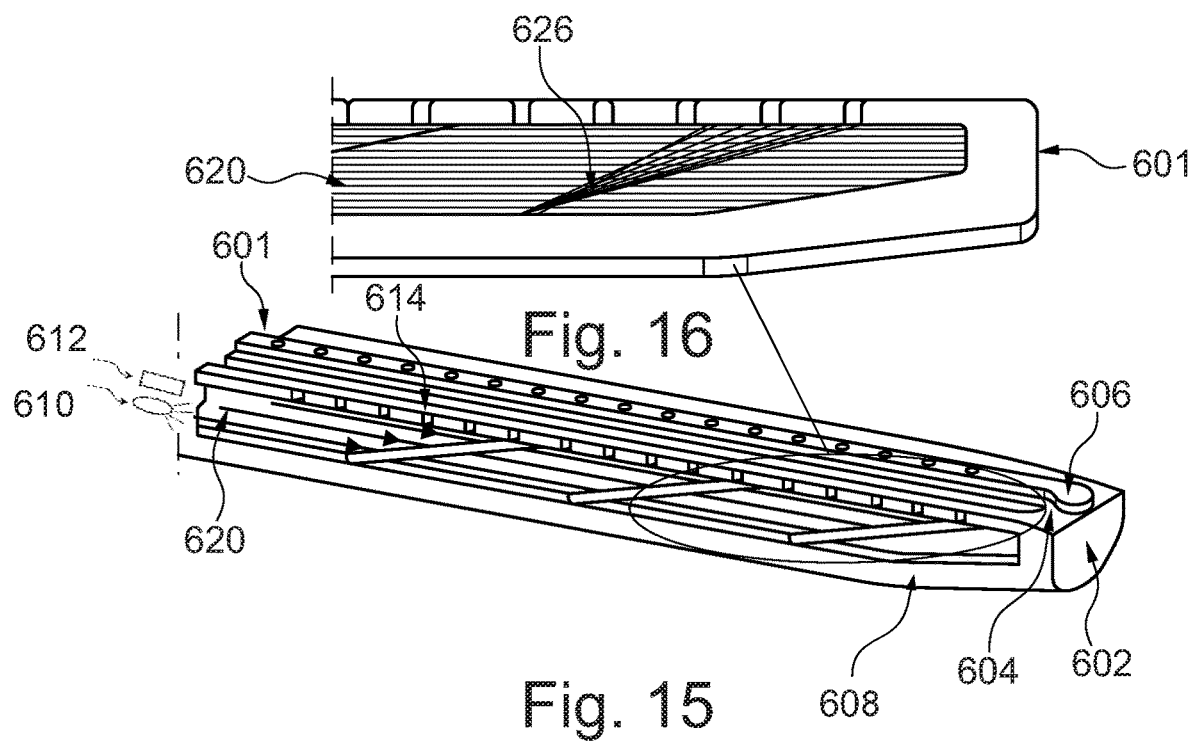
Fig. 16
Fig. 15
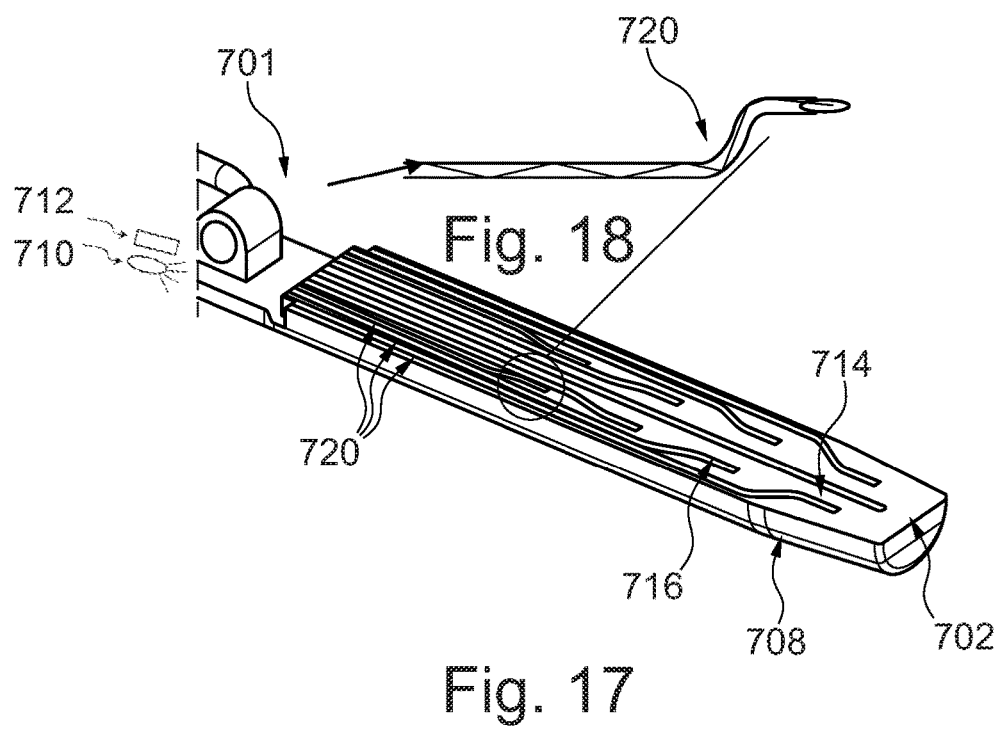
Fig. 18
Fig. 17

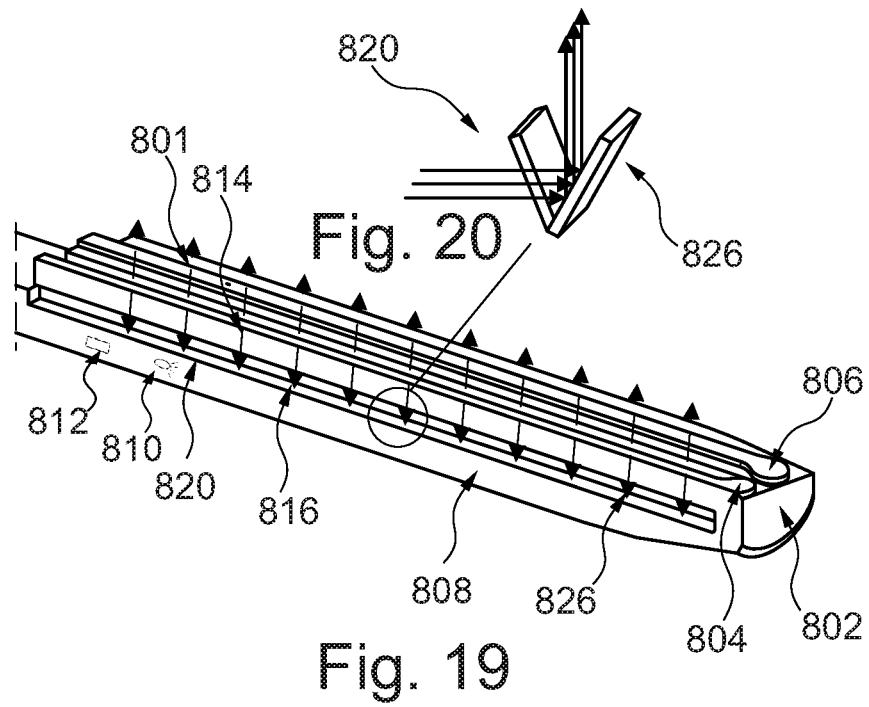
Fig. 20
Fig. 19
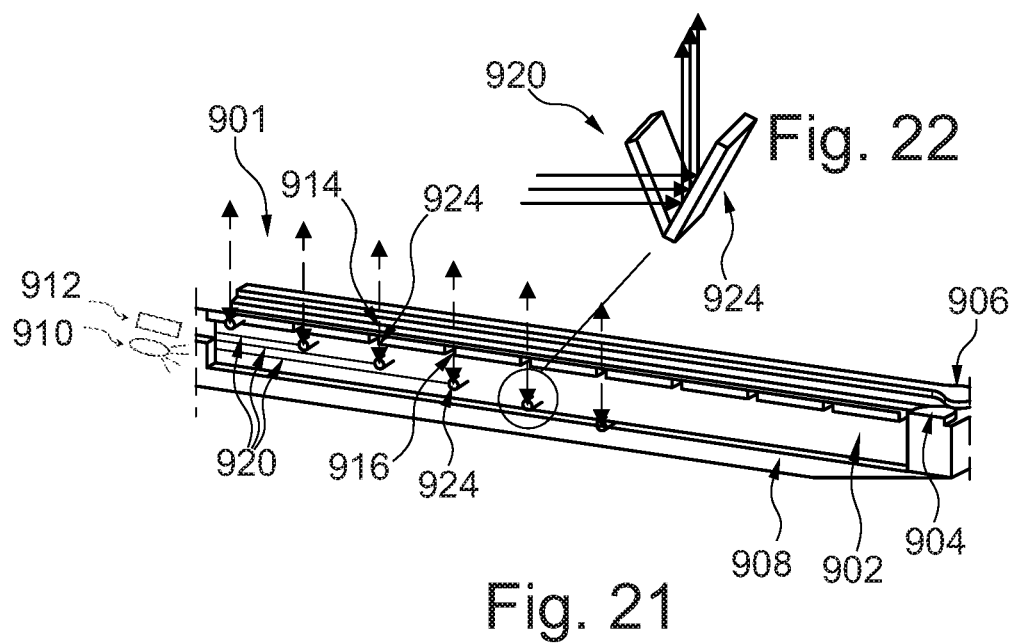
Fig. 22
Fig. 21

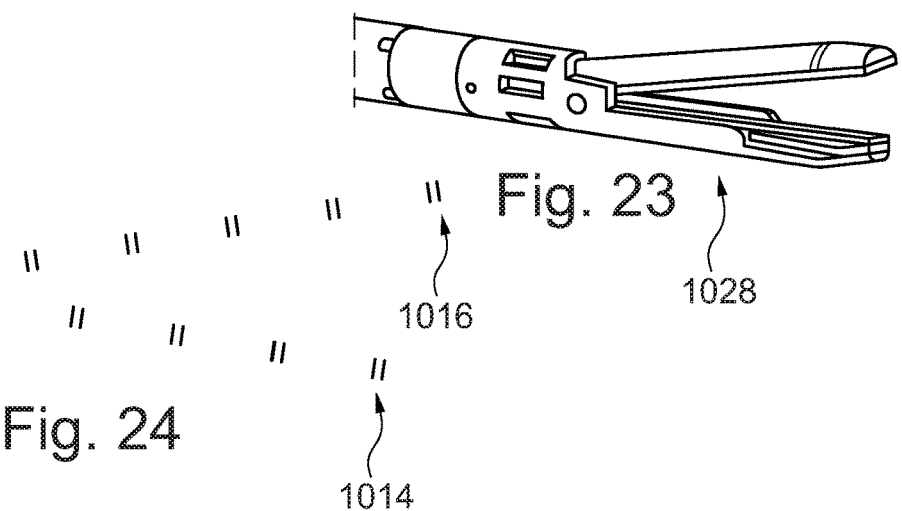
Fig. 23
Fig. 24
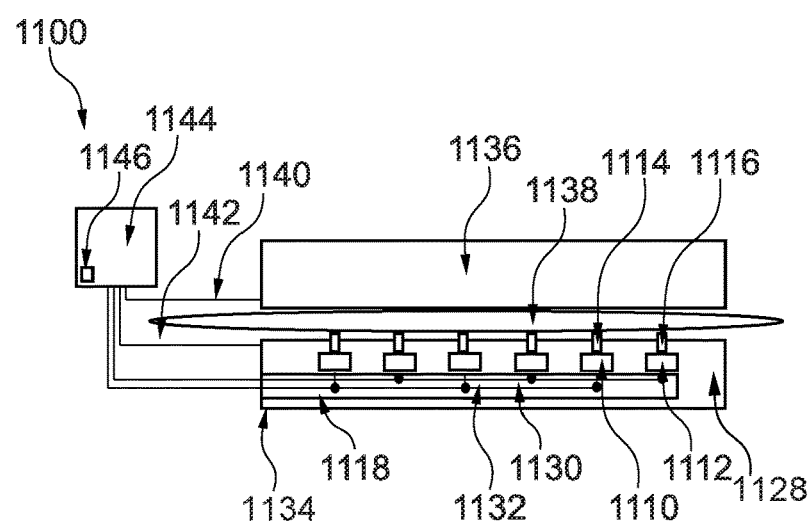
Fig. 25
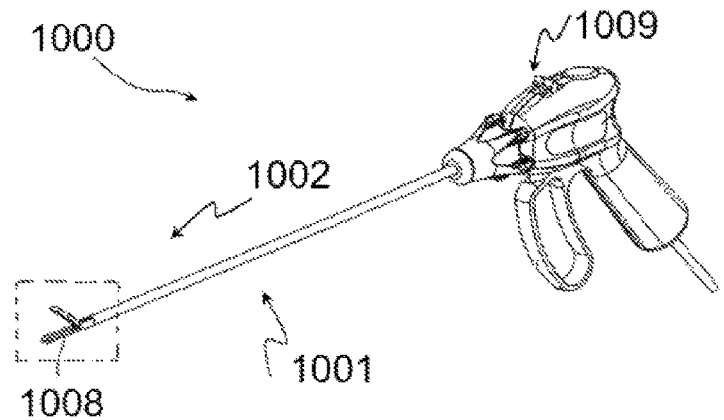
Fig. 26

DEVICE AND METHOD FOR TISSUE IDENTIFICATION

CROSS-REFERENCES TO RELATED APPLICATIONS

This application is the United States national stage entry of International Application No. PCT/EP2020/072028, filed Aug. 5, 2020, and claims priority to German Application No. 10 2019 121 365.7, filed Aug. 7, 2019. The contents of International Application No. PCT/EP2020/072028 and German Application No. 10 2019 121 365.7 are incorporated by reference herein in their entireties.

FIELD

The invention relates to a medical high frequency surgical instrument (HF, ultrasonic, laser instrument etc.) for tissue identification, in particular of human tissue, and an application of a method for tissue identification in a medical high frequency surgical instrument (HF, ultrasonic, laser instrument etc.), preferably in accordance with the present invention.

BACKGROUND

In high frequency surgery (hereinafter called HF surgery), high frequency alternating current is passed through the human body or a body part in order to selectively atrophy tissue due to the heating caused in the process (coagulation) and/or to cut it (electrotomy). The tissue damaged in this way is later resorbed by surrounding healthy tissue. An important advantage compared with conventional cutting technique with the scalpel is that simultaneously with the cut, a hemostasis by closing the vessels concerned can occur within the meaning of a coagulation. For secure closing of vessels, instruments referred to under the trademark SEAL&CUT™ should be used. The devices used are also called an electroscalpel.

Regarding the frequencies used for the HF surgery (high frequency surgery), the body tissue behaves like an ohmic resistance (impedance). The specific resistance strongly depends on the type of tissue. The specific resistance of muscle tissue and highly perfused tissue is relatively low. That of fat is approx. by a factor of 15 higher and that of bones by a factor of 1000. Frequency, shape and level of the current must/should therefore be adapted to the type of tissue on which surgery is performed.

At present, the monopolar high frequency technique is most often used in the HF surgery. In that case, a pole of the HF voltage source is connected with the patient via a counter-electrode as large as possible, for example, by contacts on the operating table on which the patient is lying, by contact bracelets or contact ankle straps respectively or by adhesive electrodes. These counter-electrodes are often called neutral electrodes. The other pole is connected to the surgical instrument which constitutes the so-called active electrode. The current is flowing via the path of least resistance from the active electrode to the neutral electrode. In close proximity of the active electrode current density is greatest, this is where the thermal effect is strongest. The current density decreases with the square of the distance. The neutral electrode should be as large as possible, and well connected to the body so that the current density in the body is kept low and no burns occur. The skin on the neutral electrode is not noticeably heated due to the large surface. When attaching the neutral electrode, strict safety measures apply. In order not to cause any burns, the correct position and a good contact of the neutral electrode (depending on the surgical area) are crucial.

In the case of the bipolar HF technique the current, contrary to the monopolar technique, is flowing through a small portion of the body—where the surgical effect (cut or coagulation) is requested. Two electrodes insulated from each other (for example, received in instrument branches) between which the HF voltage is applied, are directly guided to the surgical site. The electric circuit is closed via the tissue located in between. Within the tissue between the electrodes the thermal effect occurs.

Coagulation clamps are known. The high frequency connections are normally provided here on handle(s). As an axis for the joint serves often a screw provided with an insulating coating with which also the two clamping legs with their handles are each pivotably attached to each other.

By means of a bipolar HF vessel sealing and/or cutting system vessels or tissue bundles can be effectively and permanently sealed in general or during cutting. Hence, the lateral thermal damage of the surrounding tissue is limited and tissue adhesions are reduced to a minimum.

In medicine, tissue is defined as an organic material which consists of a group of similarly or differently differentiated cells having a common function or structure. In addition to cells, tissue also includes the extracellular matrix (ECM). Examples of human tissues are, for example, blood vessels.

The human body consists in its chemical composition of approx. 56% oxygen (O), 28% carbon (C), 9% hydrogen (H), 2% nitrogen (N), 1.5% calcium, 1% chlorine (Cl), 1% phosphorus (P), 0.25% potassium (K), 0.2% sulfur (S) and other chemical substances in smaller proportions (all data in percent by weight).

The substance composition of the human body consists of approx. 67% water, 16% proteins (for example collagens), 10% lipids (e.g. fat), 1% carbohydrates, 1% nucleic acids and 5% various minerals (all data in percent by weight).

Collagens are a group of structural proteins (a "protein" forming a bundle of fibers) found in humans and animals, mainly of the connective tissue (more precisely: the extracellular matrix).

Collagens are found, among others, in the white, inelastic fibers of tendons, ligaments, bones and cartilage. Layers of the skin (subcutaneous tissue) are also composed of collagens. In the human body, collagen is the most abundant protein, accounting for over 30% of the total mass of all proteins.

In living organisms, lipids are mainly used as structural components in cell membranes, as energy stores or as signal molecules. The term "fat" is often used as a synonym for lipids, but fats (triglycerides) are only a subgroup of lipids.

The main optical absorbers in tissues, such as, for example, in blood vessels in the NIR range, are water and collagen. The blood vessels are mostly surrounded by fat.

When electromagnetic radiation interacts with solids, liquids or gases, various effects occur, such as absorption, reflection, scattering or transmission. In other words, when electromagnetic radiation encounters an obstacle, it is either absorbed (swallowed up), scattered (deflected from its original direction), transmitted (allowed to pass through) or reflected (thrown back)—this is also referred to as remission in reflection.

In physics, remission is the diffuse (undirected) electromagnetic radiation, especially of light, which enters a scattering medium through the surface, interacts with it and exits through this surface again. This is in contrast to regular directional reflection, which satisfies the law of reflection.

However, it is more common to speak of reflection in both cases. A distinction is then made between specular and diffuse reflection. In the case of remission (diffuse reflection), part of the light is absorbed and transmitted. The surface-related measure for the remission is the reflectance.

Remission spectroscopy is a branch of spectroscopy that measures the radiation remitted by a sample. Remission spectroscopy is primarily used for the spectral investigation of opaque and insoluble samples. The measured remission spectrum of a sample consists of two parts: 1) the regular reflection, where the radiation is specularly reflected from the surface. It is described by Fresnel's equations; 2) the diffuse remission, where the radiation isotropically exits the sample in all directions. It is caused by the radiation penetrating the sample and returning to the surface after partial absorption and multiple scattering.

The respective absorption spectrum of water, collagen and fat has already been measured by numerous groups. Both in the visible spectral range (VIS) and in the near infrared spectral range (NIR), the values for the absorption coefficients are available.

In the state of the art, the control processes in bipolar HF technology are controlled by the tissue impedance, which changes in the course of the energy supply, mainly due to the loss of water. The impedance of the tissue is calculated by Ohm's law using the measured voltage and current values. Due to the configuration of an instrument, the determined impedance is always an average value of the entire system (tissue, instrument, cable, generator).

The quality of the sealing of blood vessels essentially depends on the control process and the associated energy input into the tissue. In addition to overheating of the instruments, this can also result in thermal damage to the surrounding tissue. Likewise, insufficient energy input can also lead to failure/bursting of the fused sites, which in turn becomes noticeable through bleeding. Often, this bleeding does not occur until hours after the actual surgery, so that, depending on the vessel diameter, emergency surgery can be required to stop the bleeding and/or to safely close the vessel.

It is therefore known from the State of the Art to measure the tissue temperature and to incorporate the measured temperature values into the adjustment/control of the thermal processes. In order to prevent the temperature measurement results from being distorted by the electrode temperature, a sufficiently large distance and/or thermal separation/insulation is required between the tissue temperature sensor and the electrode(s). However, this is disadvantageous in that the measured tissue temperature does not correspond exactly to the tissue temperature directly at the electrode(s).

SUMMARY

The task of the invention is therefore, in addition or as an alternative to the measurement of impedance, to enable as accurate a measurement as possible of the tissue/of the tissue composition and/or the temperature of the tissue to be fused, preferably online, in order to avoid damage to the tissue immediately at the electrode(s) and, if applicable, also to prevent overheating of the instruments. In other words, it is the task of the invention to enable good coagulation.

The invention relates to a medical high frequency surgical instrument comprising
at least one instrument branch,
at least one light source (e.g. LED) or light source assembly (e.g. LED and filter) generating a first light with a certain illumination light spectrum, which can be emitted (directly or indirectly) towards a tissue, and
at least one sensor, which is provided and adapted to detect a second light with a remission spectrum (if applicable, different from the illumination light spectrum) which is reflected by the tissue as a result of light impingement by the light source, and
to convert the second light into a detector signal according to its remission spectrum, wherein
a calculating unit (1144) is provided and configured to
receive the detector signal from the at least one sensor,
calculate a theoretical remission spectrum based on a solution for describing the light emission in the tissue, preferably based on the radiative transfer theory and its approximations, by means of the calculating unit (1144), assuming estimated volume fractions of the individual tissue components present in the tissue
adapt the theoretical remission spectrum to the measured remission spectrum by, for example, a non linear regression, a neural network or a look-up table using the calculating unit (1144), and
calculate at least one volume fraction of a tissue component from the remission spectrum via a minimization algorithm with which the theoretically calculated remission spectrum is fitted (adapted) to the measured remission spectrum by means of the calculating unit (1144) by varying the volume fractions of the individual tissue components present in the tissue.

The invention further relates to use of a tissue detection method for controlling the medical high-frequency surgical instrument with at least one instrument branch, in particular an instrument marketed under the trademark SEAL&CUT™, more preferably during a thermal procedure/process, comprising the following steps (preferably in this order):
generating a first light with an illumination spectrum/excitation spectrum, preferably in the VIS/NIR range, which can be emitted in the direction towards a tissue by means of at least one light source/illumination,
receiving the remission of the irradiated light with a remission spectrum from the tissue by at least one detector, preferably a sensor, and/or in other words, measuring a second light, which is obtained/received by remission of the irradiated first light, with a remission spectrum from the tissue by at least one sensor/detector,
converting the measured remission spectrum by means of the at least one sensor/detector into a detector signal, preferably an electrical signal/data signal,
sending the detector signal to a calculating unit, preferably a CPU,
calculating a theoretical remission spectrum based on a solution/algorithm for describing light propagation in the tissue, preferably based on radiative transfer theory and its approximations, by means of the calculating unit, preferably assuming estimated volume fractions of the individual tissue components which are present in the tissue,
adapting/fitting the theoretical remission spectrum to the measured remission spectrum, preferably by a regression, a neural network or a look-up table, by means of the calculating unit, and/or in other words, calculating at least one volume fraction of a tissue component by varying the volume fractions of the individual tissue components, which are present in the tissue, via a minimization algorithm with which the calculated theoretical remission spectrum is fitted or adapted to the measured remission spectrum, preferably by a regression, a neural network or a look-up table, by means of the calculating unit (1144), and calculating at least one volume fraction of a tissue component by varying the volume fractions of the individual tissue components, which are present in the tissue, via a minimization algorithm with which the theoretically calculated remission spectrum is fitted (adapted) to the measured remission spectrum, preferably by means of a regression, a neural network or a look-up table, by means of the calculating unit.

A thermal process is preferably any process that generates thermal effects in the tissue by releasing energy. This also includes processes which are carried out by means of high frequency, ultrasound, laser and/or temperature. It also includes processes, which are carried out by means of high-frequency, ultrasound, laser and/or temperature instruments (for example, by means of thermocautery), and/or all medical instruments which generate thermal effects in the tissue by emitting energy. Illumination spectrum or excitation spectrum preferably means the spectrum (and/or wavelength range) of the light source.

The essence of the present invention is therefore to identify tissue components by adapting/fitting calculated remission spectra to the measured remission spectrum by varying at least one parameter, if the scattering spectrum of the tissue is assumed to be known, or by varying at least two parameters, of which at least one allows a direct or indirect conclusion on the scattering of tissue and the other parameters allow a direct or indirect conclusion on the components, preferably their volume fraction, of tissue (causal relationship between the tissue components and the parameter). Preferred tissue components are water, fat and/or collagen. From the parameters obtained from the fit, it can be determined, what tissue components are present in the tissue with what volume fraction, since the absorption spectrum of the tissue calculated for the fit is combined via the characteristic components known in the tissue. In other words, it is known that water, collagen and fat are present in the tissue, therefore, by using their characteristic absorption spectra, the measured absorption spectrum can be combined as a superposition of the individual characteristic absorption spectra of the individual tissue components. Thus, by means of a fit algorithm it can be calculated in which volume fraction the individual tissue components are present.

In yet other words, the calculating unit can be used to determine in which volume fraction the individual tissue components are present in the tissue. This means that from the fit of the theoretically calculated remission spectra to the measured remission spectrum (which has been calculated by the calculating unit from the signal from the detector), the absorption spectrum of the tissue is determined independently of the scattering properties of the tissue. The absorption spectra of the individual tissue components, preferably water, fat and collagen, are stored on a storage medium in the calculating unit. Thus, the volume fractions of the tissue components can be calculated from a remission spectrum measured by the detector, an absorption spectrum calculated by the calculating unit via a linear combination of the absorption spectra of the individual tissue components with the volume fractions as prefactors, as a result of which the CPU can determine the tissue composition, hence the percentage volume fraction of the individual components.

Preferably, by means of the calculating unit, based on the calculated tissue components and/or the calculated temperature and/or the calculated tissue impedance, the current, the voltage and/or the frequency of the electrodes can be controlled and/or adjusted by the calculating unit in response to the determined tissue composition and/or the calculated temperature (based on the detector signal) and/or the calculated tissue impedance.

Preferably, the tissue identification method further comprises the following step: calculating at least one absorption maximum from the absorption spectrum by means of the calculating unit, calculating a temperature in the tissue by comparing the absorption maximum with at least one reference by means of the calculating unit, storing at least one reference in the form of an absorption maximum at a certain temperature in the calculating unit, preferably a storage medium in the calculating unit, preferably for water and/or fat and/or collagen.

Preferably, the tissue composition/the tissue components is/are an important predictable variable for the quality of a medical instrument and/or a coagulation procedure and/or an HF sealing. In particular, the collagen component is an important parameter. Preferably, it is of particular importance to adjust the process control depending on the tissue components. To determine the tissue components, the spectra/spectrum of the remission is/are preferably recorded, as in the case of a temperature measurement. That means that broadband radiation in the visible and infrared spectral range is irradiated into the tissue via an illumination, and the radiation scattered back/remitted from the tissue is detected spectrally, preferably at a distance from the irradiation location. The remission spectrum measured in this way is dependent on the scattering and absorption properties of the various tissue constituents/tissue components. By means of an algorithm/calculation method, which takes into account the scattering properties and the absorption properties, the volume fractions of the absorbing tissue components can be adapted in such a way that, by superimposing of the individual absorption spectra of the pure tissue components, an absorption spectrum is generated, with which, in conjunction with suitable scattering properties, a remission spectrum can theoretically be calculated which matches the measured remission spectrum. In this way, the water, fat and collagen content of the native tissue/the measured tissue can be determined before and/or during the process/the sealing process. If temperature-dependent spectra are used, the change in tissue composition, for example, due to evaporation of water, can also be monitored during the process. In this way, the decrease of water/of the water content in the tissue during sealing can be detected and applied as a control/adjustment and/or shutdown parameter. It could also be possible to differentiate between different types of tissue in this way.

The tissue portions of the tissue have a typical absorption characteristic. For example, water has an absorption maximum at approx. 1470 nm at room temperature, collagen, on the other hand, has an absorption maximum at approx. 1500 nm at room temperature, and fat has an absorption maximum each at 1210 nm and at approx. 1400 nm at room temperature. Preferably, the absorption maximum of water is at 1470 nm+/−20 nm, more preferably at 1470 nm+/−10 nm, most preferably at 1470 nm+/−5 nm. Preferably, the absorption maximum of collagen is at 1500 nm+/−20 nm, more preferably at 1500 nm+/−10 nm, more preferably at 1500 nm+/−5 nm. Preferably, the absorption maximum of fat is at 1210 and at 1400 nm+/−20 nm, more preferably at 1210 and at 1400 nm+/−10 nm, more preferably at 1210 and at 1400 nm+/−5 nm.

Preferably, the tissue identification method further comprises the following step:
  storing at least one reference in the form of an absorption maximum at a certain temperature in the calculating unit, preferably a storage medium in the calculating unit, preferably for water and/or fat and/or collagen.

Preferably, the calculating unit can be used to determine which temperature prevails in the tissue by using the characteristic absorption spectrum of water as a reference. It is stored on the calculating unit and/or the storage medium that water has a certain absorption maximum at a certain temperature (for example, at room temperature 1470 nm). By comparing the shift of the absorption maxima from a pre-stored value and/or by comparing with a plurality of predetermined corresponding values in a stored table, it can be determined at which wavelength of the absorption maximum which temperature prevails in the water of the tissue. The characteristic absorption spectrum of water can be determined most easily, since the tissue components in the body are known and water is the most present in the tissue with approx. 67%. Based on the measured absorption spectrum, the shift of the spectral absorption maximum of water can be calculated/determined. Based on this shift of the absorption maximum, which is approx. 0.5 nm/K, the temperature can be determined. The above is analogously applicable to fat and/or collagen and/or other components of the tissue.

The above mentioned steps for measuring the absorption spectrum can be applied analogously not only to water but also to fat, collagen or other tissue components. Thus, the individual absorption spectra of water, fat and collagen in the tissue can be determined from an absorption spectrum, which is detected by a detector and determined by a calculating unit.

Preferably, the tissue identification method further comprises the following step:
  Application of the illumination and the detector to the tissue. Advantageously, the detector and the illumination are thus in direct contact with the tissue.

Preferably, the tissue identification method further comprises the following step:
  Controlling and/or adjusting and/or switching off a device, preferably a medical instrument, by means of the calculating unit based on the calculated temperature and/or tissue impedance.

Preferably, the control and/or adjustment and/or shutdown takes place when a predetermined temperature is reached, preferably at a temperature that is greater than 85° Celsius and less than 110° Celsius, more preferably at a temperature that is greater than 95° Celsius and less than 100° Celsius. The coagulation of tissue achieves the best result at a temperature, preferably constant temperature, at a temperature which is greater than 85° Celsius and less than 110° Celsius, more preferably at a temperature which is greater than 95° Celsius and less than 100° Celsius.

Preferably, all steps take place online/in real time. This means that the controlling and/or adjustment and/or switching off of the medical instrument takes place online, preferably in real time. In other words, the absorption spectrum of the tissue is measured online, preferably in real time, which allows the temperature in the tissue to be calculated online, preferably in real time. The temperature will then be incorporated, preferably online, preferably in real time, into the control/adjustment of at least one electrode/sonotrode/laser source of the medical instrument, preferably a device marketed under the trademark SEAL&CUT™.

Preferably, the tissue identification method for temperature measurement is performed during a sealing process, more preferably in the tissue in the medical instrument.

Preferably, the detectors are provided and adapted to detect remission, preferably the remission spectra in the NIR range from 1000 nm to 1700 nm, more preferably in the range from 1400 nm to 1600 nm.

Preferably, the at least one illumination and the at least one detector are spaced apart in a medical instrument.

Preferably, a method for measuring a tissue temperature is applied in a medical instrument.

Preferably, a temperature measurement device comprises a storage medium on which at least one of the following steps is stored (preferably in this order for a plurality):
  Storing at least one reference in the form of an absorption maximum at a certain temperature in the calculating unit, preferably a storage medium in the calculating unit, preferably for water and/or fat and/or collagen.
  Applying the illumination and the detector to the tissue. Advantageously, the detector and the illumination are thus in direct contact with the tissue.
  Emitting light with an illumination spectrum, preferably in the VIS/NIR range, into a tissue by means of at least one illumination.
  Receiving the remission of light with a remission spectrum from the tissue by at least one detector, preferably a sensor.
  Converting the remission spectrum by means of the detector into a detector signal, preferably an electrical signal/data signal.
  Sending the detector signal to a calculating unit, preferably a CPU,
  Calculating the remission spectrum from the detector signal by means of the calculating unit,
  Calculating an absorption spectrum of the tissue by comparing the illumination spectrum with the remission spectrum using the calculating unit,
  Calculating at least one absorption maximum from the absorption spectrum by means of the calculating unit,
  Calculating a temperature in the tissue by comparing the absorption maximum with at least one reference, preferably stored in the calculating unit, by means of the calculating unit, and
  Controlling and/or adjusting and/or switching off a device, preferably a medical instrument, by means of the calculating unit based on the calculated temperature and/or tissue impedance.

In other words, in temperature measurement during a sealing process, remission spectra in the NIR range from 1000 nm to 1700 nm are detected online by a detector. The shift in the position of the absorption maxima, which can be derived from the recorded spectra, can be used to infer the temperature of the tissue captured in the instrument, with sufficient accuracy for the application. With increasing temperature, the position of the absorption peak shifts towards shorter wavelengths. The shift is here approx. 0.5 nm/K. If the tissue cools down further, the absorption peak shifts again towards longer wavelengths. Since the main absorber in the tissue to be sealed is water in the wavelength range around approx. 1470 nm, the temperature determined in this way reflects the temperature in the water portion of the tissue. The particular advantage of this temperature measurement method is that it can be used to measure the actual temperature in the tissue, since the NIR radiation can pass through the entire thickness of the tissue layer due to scattering. In contrast, when measuring the temperature during sealing with a thermocouple, only the temperature of the contact surface is measured. The temperature and the heat capacity of the electrodes represent a disturbance variable for the determination of the tissue temperature with this method. This leads to latency times and distortions of the true tissue temperature. Therefore, this method does not reflect the tissue temperature, but represents the temperature of the environment with which the thermocouple is in contact. With the optical temperature determination it is possible to obtain important parameters for the control of the sealing process. Furthermore, the determined temperature can be used as a shutdown/control/adjustment criterion/process parameter and/or for process control/process adjustment.

It has been shown that light preferably of a certain wavelength (for example, white light in the VIS-NIR range) is remitted from the body tissue, wherein the spectrum of light remitted from the body tissue changes as a function of temperature. It is therefore possible to bring an illumination/illumination output for irradiation of body tissue as well as a detector/detector input for detection of light remitted by the body tissue directly to the electrode(s), and thus determine the tissue temperature in the immediate vicinity of (between) the electrode(s) via the detour of the detected remitted light and its spectral distribution.

Accordingly, in the preferred embodiment, a medical instrument (of the HF type) comprises
at least one instrument branch, which forms at least one energizable electrode for sealing and/or cutting tissue or is arranged in or at the at least one energizable electrode for sealing and/or cutting tissue, wherein the energization of the electrode is controllable and/or adjustable by a calculating unit, and
at least one temperature measurement device comprising at least one illumination and at least one light detector, each of which is/are (alternately) formed or arranged in or on the at least one instrument branch or in opposite position in/on two instrument branches, and which are in electrical connection with the calculating unit. In other words, on one instrument branch an illumination and a detector are alternately arranged, respectively, wherein on the opposite instrument branch an illumination is opposite to the illumination and a detector is opposite to the detector.

According to one aspect, a plurality of detectors are formed or arranged alternately on two opposite instrument branches, and are in electrical communication with a calculating unit. This means in other words that each an illumination and a detector are alternately arranged on one instrument branch, wherein, on the opposite instrument branch, an illumination is opposite to the illumination and a detector is opposite to the detector, in order to reduce or to avoid a measurement distortion at the respective detector by light entering on the opposite side.

The medical instrument is a surgical instrument, a monopolar instrument, a bipolar instrument, an electrosurgical instrument, a surgical clip, a surgical clamp, a surgical forceps, surgical scissors, a scalpel, and/or the like. More preferably, the medical instrument is an instrument marketed under the trademark SEAL&CUT™ which is provided and adapted to cut and simultaneously seal tissue by means of HF technology. Monopolar instruments have the advantage that by being formed in a single shell (only a single instrument branch), a compact design is made possible, and thus lower costs in their to manufacture. Bipolar instruments (two opposite instrument branches) have the advantage that a resolved analysis is more feasible, and that they are more variable in the implementation of duplication.

Preferably, the at least one instrument branch is to be understood as the part/the end of a medical instrument, the distal part of which is an instrument branch body and/or a tissue engaging portion (branch body), which can be brought into contact with the tissue, and the proximal part of which is formed as an actuating portion or grip portion. More preferably, the at least one instrument branch is a jaw branch. The instrument branch body of the at least one instrument branch can be formed as an electrode for sealing tissue, preferably the instrument branch body is integrally formed/made of a single part out of a conductive metal or graphite in this case. Alternatively, the electrode can be formed/arranged/embedded in and/or at and/or on the instrument branch, preferably in this case the instrument branch body is made out of an insulator and/or electrically insulating material.

Preferably, the medical instrument has two opposing instrument branches, which are preferably movable/pivotable towards each other, at the ends of which facing sides/jaws/areas/instrument branch ends/instrument branch bodies are arranged/formed, which can be brought into contact with the tissue. The instrument branch ends/instrument branch bodies can themselves be formed as electrodes for sealing tissue. Preferably the instrument branch ends/instrument branch bodies are made in this case of a conductive metal or graphite, and are insulated from each other. But the electrodes can also be formed/arranged/embedded in and/or at and/or on the instrument branch ends/instrument branch bodies. Preferably, the instrument branch ends/instrument branch bodies are in that case made of an insulator and/or electrically insulating material or they are made of metal, and insulated against the electrodes.

Preferably, at least one electrode is controllable and/or adjustable by the calculating unit. More precisely, the current intensity, the voltage, the phase and/or the frequency of the electric current applied to the electrode is controllable or adjustable.

Preferably, the temperature measurement device is an optical temperature measurement device/a thermometer with an optical transmitter in the form of an illumination and an optical receiver in the form of a light detector.

Preferably, illumination means at least one light source/excitation light source and, alternatively, in addition other optical components, such as, for example, a light tunnel comprising optical waveguides/mirrors/lenses/reflecting inner walls/scattering media and the like. More preferably, light source means a white light source/an LED (in the VIS and/or IR and/or UV range), a deuterium lamp (UV range) and/or a halogen lamp (VIS range).

In other words, the light at/in/on the instrument branch at the irradiation location/at the at least one entrance opening can be generated directly by means of a light source, or by guiding the light from a light source by means of optical waveguides/mirrors/lenses/light tunnels/scattering media and the like to an irradiation location/a light inlet opening/a light entrance opening of the contact surface of the instrument branch which is provided and adapted to come into contact with the tissue. More preferably, the irradiation of the light of the illumination takes place at a certain angle relative to the tissue contact surface of the corresponding instrument branch and/or electrode, that means that the illumination has an angled/oblique exit opening and/or light radiation in/at/on the instrument branch. In yet other words, the light source itself is arranged obliquely/angled on/at/in the instrument branch or has an oblique/angled surface with respect to the tissue contact surface and/or the light emitting surface. Alternatively, an optical element, such as, for example, a mirror and/or an optical waveguide can be arranged obliquely on/at/in the contact surface (the surface which is provided and adapted to come into contact with the tissue) of the instrument branch and guide the light from the light source to the irradiation site and/or the contact surface.

A white light source, hence, a light source, which emits electromagnetic radiation over the entire VIS range, has the advantage that more information can be obtained from the tissue to be illuminated, as a result of which a tissue identification and/or multivariate data analysis are possible. Furthermore, it is possible to perform a variety of different measurements. For example, on the instrument branch at least one illumination with a white light source and at least one detector can be arranged, which is provided and adapted to measure spectral ranges, preferably with different sensors (Si, InGaAs sensors, etc.).

A light source with a low spectral bandwidth has the advantage that the implementation is simple, that such a light source is inexpensive, that a high temporal scanning can be achieved with such a light source and that distances of more than 2 mm from each other and/or from a detector are possible, since a higher intensity with respect to a certain spectral range is possible.

Preferably, by detector and/or light detector is meant at least one sensor/a photodiode and/or a photomultiplier (PMT) and, if applicable, other optical components, such as, for example, a light tunnel which can comprise optical waveguides/mirrors/lenses//reflective inner walls/scattering media and the like. In other words, the light from the detector/detector part, installed in/at/on the instrument branch, at the remission location can be measured directly by means of a sensor of the detector or the like, located there, at/in/on the instrument branch, or via a light tunnel, which can comprise optical waveguides/mirrors/lenses/reflective inner walls/scattering media and the like, and light can be guided from the contact surface/a light entrance opening of the instrument branch to a sensor or the like, arranged remotely from the contact surface of the instrument branch or even remotely from the instrument branch. More preferably, the irradiation of the light starting from the illumination occurs at a certain angle (0°<angle≤90°) relative to the tissue contact surface of the corresponding instrument branch and/or electrode. More preferably, the detector in/at/on the instrument branch has an entrance opening which is also angled/oblique relative to the contact surface. In yet other words, the detector itself is arranged obliquely/angled on/at/in the instrument branch or has an oblique/angled surface with respect to the tissue contact surface. Alternatively, an optical element, such as, for example, a mirror and/or an optical waveguide can be arranged obliquely on/at/in the contact surface (the surface which is provided and adapted to come into contact with the tissue) of the instrument branch and guide remission light to a remote sensor or the like. The light remitted from the body tissue after irradiation is preferably spectrally resolved into at least two channels (by means of spectrometers, prisms or different filters) and is then detected by the at least two sensors or the like, which contingent thereon are sending at least two signals to the calculating unit/CPU which transforms the at least two signals into a temperature value.

The electrode for sealing tissue is preferably made of metal, conductive ceramic, metallized ceramic, graphite or metallized graphite. The electrode is more preferably formed with a surface which is provided and adapted to reflect electromagnetic radiation.

The calculating unit preferably comprises a processor and a storage medium. The storage medium is provided and adapted to store steps for performing the measurement of the temperature and/or the control and/or adjustment of the current of the electrode.

The calculating unit controls the illumination/light source of the illumination (duration, intensity, wavelength, etc.) by means of a first electrical signal, and the detector detects the light scattered/reflected (exclusively) by the body tissue and/or the remission directly on the tissue to be measured/to be treated (between the instrument branches), and is sending the acquired data as a second electrical signal to the calculating unit. The calculating unit now calculates, by means of an algorithm on the storage medium, the temperature of the tissue which can be derived from the respective second electrical signal. On the basis of the temperature of the tissue calculated in this way, it is calculated online/in real time which current intensity, which voltage and/or frequency the electric current should have which is applied to the at least one electrode.

In addition, in one embodiment, the resistance of the tissue (tissue impedance) can also be determined by the calculating unit, and can be included in the calculation. In other words, the tissue impedance of the tissue at/between the electrodes/sonotrodes can be determined, so that the current intensity, voltage and/or frequency of the electric current applied to the electrode(s) or the US transducer can be controlled or adjusted by the calculating unit in response to the determined tissue impedance and (in combination with) the second signal of the (optical) temperature measurement device.

Preferably, the calculating unit is connected to the (optical) temperature measurement device according to the invention in such a way that the current intensity, the voltage and/or the frequency of the electric current applied to the at least one electrode can be changed in response to the temperature calculated by the calculating unit/CPU, preferably automatically and/or by a predetermined algorithm.

Preferably, the second electrical signal from the detector corresponds to a light spectrum which represents the wavelength and the intensity of the light detected at the detector. On the basis of this spectrum, the shift of the spectral absorption maximum of water is calculated/determined. By means of this shift of the absorption maximum, which is approx. 0.5 nm/K, the temperature can be determined. Since the absorption spectrum of water is characteristic, the shift can also be determined without reference measurement and/or with reference measurement.

Preferably, the calculating unit is configured in such way that it comprises at least one of the following steps or at least one of the following steps is stored on a storage medium in the calculating unit (preferably in the following order):

Controlling the illumination by the calculating unit with a first electrical signal, preferably with an electrical current with a certain current intensity and/or a certain voltage and/or a certain frequency, Emitting an electromagnetic radiation of the illumination (preferably white light) into the tissue in a certain area in the immediate vicinity of an electrode or between two electrodes facing each other, Measuring (by means of the detector) the remission/diffuse reflection of the electromagnetic radiation starting from the body tissue, Sending the measurement results from the detector to the calculating unit by means of a second electrical signal, Transforming the second electrical signal into a tissue temperature value, Preferably determining the tissue impedance, preferably between two electrodes, and Processing the tissue temperature value, and preferably the determined tissue impedance by means of the calculating unit, preferably by means of a pre-programmed algorithm on the storage medium, to determine a new current intensity, voltage and/or frequency for the electrical current applied to the electrode(s), in order to reach or approach a temperature of the tissue of above 95° Celsius and preferably simultaneously of below 100° Celsius.

In one embodiment, the light tunnel, which is in communication with the light source, can be fed at least one end by at least one light source, and the at least one other end can terminate in the instrument branch. In other words, light from at least one light source can be directed via an optical waveguide or the like to at least one output which is located at/on/in the instrument branch. Alternatively, at least one light source, for example, the LED, can be located/arranged directly on/at/in the instrument branch.

In one embodiment, the light tunnel, which is in communication with the detector, can comprise at least one sensor at at least one end and terminate in the instrument branch at the at least one other end. In other words, light/remission from at least one input, which is located on/in the instrument branch, can be directed to at least one sensor/a photodiode/a photomultiplier or the like via a reflective light channel/an optical waveguide or the like. Alternatively, at least one sensor/photodiode/photomultiplier can be located on/at/in the instrument branch.

Preferably, the illumination and the detector can share one end of a light tunnel. In other words, the beam path of the light source and the beam path of the sensor/photodiode/photomultiplier can share a light tunnel, so that both are in optical contact with the body tissue via a single optical aperture which simultaneously forms the entrance and the exit of the light on/at/in the instrument branch.

Preferably, a plurality of detectors and a plurality of illuminations are arranged on at least one instrument branch. In this regard, the detectors and/or illuminations can each be arranged on an instrument branch in a predetermined pattern. Preferably, the pattern is linear. Alternatively, at least one detector and/or one illumination can be arranged on a first instrument branch, and at least one detector and/or one illumination can be arranged on a second instrument branch, preferably on facing sides of opposite instrument branches. In other words, in this embodiment for bipolar instruments, light can be introduced into the tissue from an illumination device and on an opposite side a detector can measure the light remitted from the tissue.

Preferably, the distance between the at least one illumination and the least one detector is between 0 and 5 mm, more preferably between 0 and 1 mm, since the intensity of the remission is very high in this location.

Preferably, the at least one instrument branch has multiple detectors per illumination, more preferably, the detectors are arranged at equal and/or different distances from the illumination. In other words, the distance from an illumination to a second detector can be greater than the distance to a first detector.

Preferably, the illumination has a discrete light source, preferably with a defined bandwidth, more preferably with a bandwidth smaller than 100 nm.

Preferably, the (optical) temperature measurement device is arranged on a plane of the instrument branch which is located lower than the contact surface of the electrode. In other words, a contact surface of the electrodes and/or the instrument branches, which comes into contact with tissue, forms a plane. This plane is located higher (closer to the tissue) in the contact direction than the plane on which the at least one illumination and/or the at least one detector is arranged.

Preferably, the (optical) temperature measurement device permits a real time/online determination of the temperature during a sealing process/sealing. The online determination is of particular importance for the quality of the sealing. The measurement represents in this case the temperature in the tissue/the tissue temperature and has no latency time or distortion of the measured temperature by the heat capacity of the measuring device, for example, by the heat capacity of electrodes made of metal. The advantage of an optical temperature measurement, which is sensitive to the water in the tissue being grasped/coming into contact is that this temperature measurement device has no significant heat capacity.

Preferably, the remission measurement in the instrument branch and/or in the jaw of an instrument marketed under the trademark SEAL&CUT™ can be performed independently of the position at which the tissue comes into contact with the instrument branch. In other words, the temperature measurement device is arranged in a distributed manner, preferably uniformly distributed, on the surface of the instrument branch in the area, which is provided and adapted to come into contact with the tissue. As it has been set forth above, the at least one instrument branch can have a plurality of excitation and detection paths/illumination or detection paths, preferably along and/or in an electrode.

As it is explained above, in addition or alternatively to the measurement of the impedance, a measurement of the temperature shall be performed. The temperature is measured directly in the tissue to be fused, preferably between two opposite instrument branches, and preferably in the (temporal) course of the energization/heating of the tissue. Hereby, the change of the tissue state can be detected directly/online and thus one can also react to it. By extending the algorithm by a further control/adjustment parameter, it is possible to better evaluate the energy input into the tissue, and thus to better control/adjust the fusion of the tissue. In addition, the temperature measurement device according to the invention can also be used to measure other properties of the tissue, for example, the water portion/the water content in the tissue.

Preferably, the electrode has at least a first electrode surface on the surface, which is provided and adapted to come into contact with the tissue. Preferably, the electrode is located on an instrument branch body (in the jaw) of an instrument branch or is formed by the instrument branch. Preferably, at least one light source/at least one light guide/at least one optical component (dichroic mirror/beam splitter/mirror) and/or at least one light detector (or a part thereof) with at least one sensor and, if applicable, a light guide are incorporated in the electrode and/or the instrument branch. A photodiode or a photomultiplier can also be understood as a sensor. Preferably, the electrode has at least one light exit opening from/through which the light of the light source radiates out of the electrode surface and/or into the tissue. Preferably, the electrode has at least one light entrance opening through which the light is radiated/remitted/reflected (exclusively) from the tissue (remission) into/through the electrode surface into the sensor. Preferably, the electrode preferably comprises at least one channel, which is provided and adapted to guide data by means of at least one cable/electrical line to at least one calculating unit, or to conduct light by means of at least one scattering medium/at least one optical waveguide/at least one reflecting surface, to a remote sensor, which in turn guides data by means of at least one cable/electrical line to at least one calculating unit. If the invention has more than one electrode surface and/or more than one instrument branch, the electrode surfaces/instrument branches are spaced apart from each other, preferably in parallel. The space between the electrode surfaces/instrument branches is preferably provided and adapted to receive in an insertable manner a cutting device, such as a knife, a scalpel, an HF scalpel or the like, which is provided and adapted to separate/cut tissue. Thus, on the at least two sides of the cut of the tissue, the electrode/branch surfaces are formed to coagulate the tissue by means of HF technique.

A narrow-band filter is preferably arranged in front of the sensor. A light tunnel can be formed in the electrode and/or the instrument branch. In other words, the light tunnel can guide light through the instrument branch and/or the at least one electrode. All embodiments can be combined with each other.

The invention is explained in more detail below by means of preferred embodiments with reference to the accompanying drawings.

BRIEF DESCRIPTION OF THE DRAWING FIGURES

FIG. 1 shows an area of an instrument branch according to a first embodiment.

FIG. 2 shows a first illumination and detection arrangement of an instrument branch.

FIG. 3 shows a second illumination and detection arrangement of an instrument branch.

FIG. 4 shows a third illumination and detection arrangement of an instrument branch.

FIG. 5 shows an area of an instrument branch according to a second embodiment.

FIG. 6 shows the light guidance in the area of the instrument branch according to the second embodiment.

FIG. 7 shows an area of an instrument branch according to a third embodiment.

FIG. 8 shows the light guidance in the area of the instrument branch according to the third embodiment.

FIG. 9 shows an area of an instrument branch according to a fourth embodiment.

FIG. 10 shows the light guidance in the area of the instrument branch according to the fourth embodiment.

FIG. 11 shows an area of an instrument branch according to a fifth embodiment.

FIG. 12 shows the light guidance in the area of the instrument branch according to the fifth embodiment.

FIG. 13 shows an area of an instrument branch according to a sixth embodiment.

FIG. 14 shows the light guidance in the area of the instrument branch according to the sixth embodiment.

FIG. 15 shows an area of an instrument branch according to a seventh embodiment.

FIG. 16 shows the light guidance in the area of the instrument branch according to the sixth embodiment.

FIG. 17 shows an area of an instrument branch according to an eighth embodiment.

FIG. 18 shows the light guidance in the area of the instrument branch according to the eighth embodiment.

FIG. 19 shows an area of an instrument branch according to a ninth embodiment.

FIG. 20 shows the light guidance in the area of the instrument branch according to the ninth embodiment.

FIG. 21 shows an area of an instrument branch according to a tenth embodiment.

FIG. 22 shows the light guidance in the area of the instrument branch according to the tenth embodiment.

FIG. 23 shows a bipolar instrument branch according to the above embodiments.

FIG. 24 shows opposite detectors and illuminations on a bipolar HF instrument.

FIG. 25 shows a schematic diagram of a medical device according to the invention.

FIG. 26 shows an example of a medical high frequency surgical instrument according to the invention.

DETAILED DESCRIPTION

FIG. 1 shows an area of an instrument branch 1 according to a first embodiment. The instrument branch 1 has at least one electrode 2, embedded in the instrument branch 1 in an insulated manner. The electrode 2 has a first electrode surface 4 and a second electrode surface 6 on the branch side which is provided and adapted to come into contact with a body tissue. The electrode(s) 2 is/are located in particular in/on an instrument branch body 8 of the instrument branch 1, which constitutes one half of an operable instrument jaw. Alternating light sources (LEDs) 10 and light detectors and/or sensors 12 are incorporated into the electrode 2 and/or into the instrument branch 1/the instrument branch body 8. The electrode 2 and/or the instrument branch 1/the instrument branch body 8 has light exit openings 14 through which the light from the light source 10 radiates from the electrode surface 4 and/or 6 and/or the branch contact surface into the tissue. The electrode 2 and/or the instrument branch 1/the instrument branch body 8 moreover has light entrance openings 16 through which the light is remitted from the tissue into/through the electrode surface 4 and/or 6 and/or through the branch contact surface into the sensor 12. The electrode 2 and/or the instrument branch 1/the instrument branch body 8 has at least one (longitudinal) channel 18, which is provided and adapted to transmit data/signals from the sensors 12 by means of a cable (not shown in more detail) to a calculating unit (not shown in more detail).

FIG. 2 shows a first variant of an illumination and detection arrangement of instrument branch 1. Each one of the embodiments of the present application can comprise the first illumination and detection arrangement. The upper row of the illumination and detection arrangement of FIG. 2 is arranged/embedded at/in the second electrode/branch surface 6 of FIG. 1. The lower row of the illumination and detection arrangement of FIG. 2 is arranged/embedded at/in the first electrode/branch area 4 of FIG. 1. A detector/sensor 12 and an illumination/light source 10 are each arranged alternately in each row. The dark dots represent a detector/sensor 12 and the light dots represent an illumination/light source 10 here. Preferably, a narrow band (light) filter (not shown) is arranged in front of the detector/sensor 12. More preferably, the optoelectronic components (sensor 12 and illumination 10) are mounted on a circuit board below the electrode/below the tissue contact surface of the branch.

FIG. 3 shows a second variant of an illumination and detection arrangement of an instrument branch. Each one of the embodiments of the present application can comprise the second variant of an illumination and detection arrangement. In this case, the dark dots represent a sensor 12 and the light dots represent a light source 10. The second variant of an illumination and detection arrangement is configured in such a way that that four sensors 12 each are arranged around a light source 10 at an equal distance from the light source 10, wherein the one light source 10 shares two sensors 12 each with another directly adjacent light source. In other words, the/each light source 10 is located in the center of an imaginary rectangle, at the corners of which the sensors 12 are positioned.

FIG. 4 shows a third variant of an illumination and detection arrangement of an instrument branch. Each one of the embodiments of the present application can comprise the third variant of an illumination and detection arrangement. In this case, the dark dots represent a sensor 12 and the light dots represent a light source 10. The third variant of an illumination and detection arrangement is the same as the first variant of an illumination and detection arrangement, except that the row of the illumination and detection arrangement of the second electrode/branch surface begins where the row of the illumination and detection arrangement of the first electrode/branch surface ends.

FIG. 5 shows an area of an instrument branch 101 according to a second embodiment. The instrument branch 101 comprises an electrode 102. The electrode 102 has on the (branch) surface, which is provided and adapted to come into contact with the tissue, a first electrode surface 104 and a second electrode surface 106. In this respect, the branch of the second embodiment corresponds to the branch of the first embodiment. The electrode 102 is located in particular on a distal instrument branch body 108 of the instrument branch 101 which is a portion of an instrument jaw. Light sources 110 and sensors 112 (not shown in detail) are integrated into the instrument branch 101, for example, in an actuating portion or grip portion of the instrument branch 101, remote from the tissue contact surface of the instrument branch body 108. The electrode 102/the instrument branch body 108 comprises light exit openings 114 through which the light from the light source is directed and from which light radiates into/enters the tissue from the electrode surface 104 and/or 106 and/or the tissue contact surface of the instrument branch body 108. The electrode 102/instrument branch body 108 comprises light entrance openings 116 through which the light radiates/enters from the tissue into/through the electrode surface 104 and/or 106 and/or tissue contact surface of the instrument branch body 108 into a light tunnel 120 which terminates in the sensor. Light from the light source to the light exit opening 114 is also directed through a light tunnel 120, preferably a different light tunnel 120. The light tunnels 120 are filled with air or another gas or have a vacuum. The light tunnels 120 pass through the instrument branch body 108 and/or through the electrode 102. The, preferably cylindrical, light tunnels 120 have an inner tunnel surface (in hollow cylindrical shape) which in turn has reflective properties for electromagnetic waves (light waves). The tunnel surface on the tunnel inner side is thus provided and adapted to allow total reflection.

FIG. 6 shows the light guidance in the area of the instrument branch/the instrument branch body according to the second embodiment in the light tunnel 120. The incoming light coming from the light source is totally reflected at the inner surface of the light tunnel 120, and can thus be guided through the light tunnel 120. Due to the total reflection on the inner side of the light tunnel 120, the light can also be guided through bent areas/at least one bend or the like. In this case, the light tunnel 120 is guided along the branch body 108 in order to then reach the tissue contact surface of the branch body 108 in a substantially 90° bend (or another angle with respect to the tissue contact surface), where the light tunnel 120 opens.

FIG. 7 shows an area of an instrument branch 201 according to a third embodiment. The instrument branch 201 comprises an instrument branch body 208, which forms a portion of an instrument jaw, which is an electrode or in which an electrode 202 is embedded in an insulating manner, as shown in FIG. 7. The electrode 202 has a first electrode surface 204 and a second electrode surface 206 on the branch surface, which is provided and adapted to come into contact with the tissue. Accordingly, the electrode 202 is located on/in the instrument branch body 208 of the instrument branch 201. Light sources 210 and sensors 212 are integrated into the instrument branch 201, for example, in an actuating portion or grip portion of the instrument branch 201, remote from the tissue contact surface (not shown in detail). The electrode 202 and/or the instrument branch body 208 has light exit openings 214 through which the light from the light source, which is not shown, is directed and from which light radiates/enters into the tissue from the electrode surface 204 and/or 206 and/or the tissue contact surface. The electrode 202 and/or the instrument branch body 208 has light entrance opening 216 through which the light radiates/enters from the tissue into/through the electrode surface 204 and/or 206 and/or the tissue contact surface of the instrument branch body 208 into a light tunnel 220 which terminates in a sensor. Light from the light source to the light entrance opening 216 is also directed through a light tunnel 220, preferably a different light tunnel 220. The light tunnels 220 are filled with air or another gas or have a vacuum. The light tunnels 220 pass through the instrument branch body 208 and/or through the electrode 202. The light from the light source is introduced/irradiated perpendicular to the opening of the, preferably cylindrical, light tunnel 220/to the longitudinal direction of the cylindrical light tunnel 220. The light is thus guided straight/in a straight line in the light tunnel 220. To direct the light, at least one mirror and/or a prism is used in the light tunnel 220 in order to deflect/guide the light at a desired angle. The tunnel 220 can take any geometric shape, for example, cylindrical, cuboid-shaped, etc.

FIG. 8 shows the light guidance in the area of the instrument branch according to the third embodiment in the light tunnel 220. The incoming light coming from the light source is fed into the light tunnel 220 in a straight line/in a directional manner/in a parallelly directed manner. Due to guidance by means of at least one mirror in the light tunnel 220, the light can also be guided over angled areas/angles or the like.

FIG. 9 shows an area of an instrument branch 301 according to a fourth embodiment. The instrument branch 301 has an electrode 302, which is received in an instrument branch body 308, which forms a tissue contact surface. The electrode 302 has a first electrode surface 304 and a second electrode surface 306 on the surface which is provided and adapted to come into contact with the tissue. Thus, the electrode 302 is located in/on the instrument branch body 308 of the instrument branch 301. In the instrument branch 301, for example, in an actuating portion or grip portion of the instrument branch 301, light sources and sensors are provided remotely from the tissue contact surface of the instrument branch body 308 (not shown in detail). The electrode 302 and/or instrument branch body 308 has light exit opening 314 through which the light from the light source, which is not shown, is directed and from which light radiates into/enters the tissue from the electrode surface 304 and/or 306 and/or the instrument branch body 308. The electrode 302 and/or the instrument branch body 308 has light entrance openings 314 (not shown) through which the light radiates/enters from the tissue in/through the electrode surface 304 and/or 306 and/or through the contact surface of the instrument branch body 308 into a light tunnel 320 which terminates in a sensor. Light from the light source to the light exit opening 314 is also directed through a, preferably different, light tunnel (not shown). The light tunnels 320 are filled with a diffusing bulk material 322. The light tunnels 320 pass through the instrument branch body 308 and/or through the electrode 302. In this embodiment, at least two light tunnels 320 are arranged in parallel in the electrode 302 and/or the instrument branch body 308 in a row/line such that a row of light entrance openings 314 and light exit opening (not shown) are each provided in a respective electrode surface 304 and 306. In an embodiment not shown, the bulk material of the fourth embodiment can itself be a light source, that means that the bulk material can glow.

FIG. 10 shows the light guidance in the area of the instrument branch according to the fourth embodiment in a light tunnel 320. The incoming light coming from the light source is fed into the light tunnel 320, more specifically into the diffusing and/or luminous bulk material 322 in the light tunnel 320. Due to the scattering of the light in the bulk material 322, the light is radiated into the tissue and the remitted light is guided/scattered to the sensor by another light tunnel (not shown) having the same structure.

FIG. 11 shows a portion of an instrument branch 401 according to a fifth embodiment. The instrument branch 401 has an electrode 402 which is in this case embedded in an instrument branch body 408 in an insulating manner. The electrode 402 has on the surface of the instrument branch body 408, which is provided and adapted to come into contact with the tissue, a first electrode surface 404 and a second electrode surface 406. Thus, the electrode 402 is located in/on the instrument branch body 408 of the instrument branch 401. In the instrument branch 401, for example, in an actuating portion or grip portion of the instrument branch 401, light sources 410 and sensors 412 are provided remotely from the tissue contact surface of the instrument branch body 408 (not shown in detail). The electrode 402 and/or the instrument branch body 408 comprises light exit openings 414 through which the light from a light source not shown is directed and from which light radiates into/enters the tissue from the electrode surface 404 and/or 406 and/or from the tissue contact surface. The electrode 402 and/or the instrument branch body 408 has light entrance openings (not shown) through which light from the tissue radiates/exits in/through the electrode surface 404 and/or 406 and/or through the tissue contact surface into a light tunnel 420 which terminates in a sensor. Light from the light source to the light exit opening 414 is also directed through a, preferably different, light tunnel (not shown). The light tunnels 420 are filled with a textured bulk material 422. The light tunnels 420 pass through the instrument branch body 408 and/or through the electrode 402. In this embodiment, at least two light tunnels 420 are arranged in parallel in the electrode 402 and/or the instrument branch body 408 in a row/line, such that a row of light entrance openings 414 and light exit openings (not shown) are each provided in a respective electrode surfaces 404 and 406. In an embodiment not shown, the bulk material of the fifth embodiment can itself constitute a light source, that means, the bulk material can glow.

FIG. 12 shows the light guidance in the area of the instrument branch according to the fifth embodiment in a light tunnel 420. The incoming light coming from the light source is fed into the light tunnel 420, more specifically into the structured bulk material 422 in the light tunnel 420. Due to the structure of the insert in the bulk material 422, the light is radiated into the tissue and the remitted light is guided/scattered to a sensor by another light tunnel (not shown) having the same structure.

FIG. 13 shows an area of an instrument branch 501 according to a sixth embodiment. The instrument branch 501 has an electrode 502, wherein in this embodiment, the instrument branch body 501 and the electrode 502 correspond to the previous embodiments in terms of their structure and arrangement. Light sources 510 and sensors 512 are integrated into the instrument branch body 508 (not shown in detail). The electrode 502/the instrument branch body has light exit openings 514 through which the light from a light source is directed and from which light radiates into/enters the tissue. The electrode 502/the instrument branch body comprises light entrance openings (not shown) through which the light from the tissue radiates/enters into a light tunnel 520 which terminates in a sensor. The light from the light source to the light entrance opening 514 is directed through at least one light tunnel 520. In this embodiment, a single light tunnel 520 is formed in the electrode 502 and thus in the instrument branch body 501. A row each of light exit openings 514 and light entrance openings (not shown) is provided in the electrode 502 and/or in the instrument branch body. At least one mirrored/reflective oblique/angled plane 524 is formed in the light tunnel 520. The plane 524 can be formed by polishing the electrode and/or instrument branch body, or by introducing a mirror into the light tunnel 520. The light tunnel 520 passes through the instrument branch body. At least one row of light exit openings 514 and light entrance openings (not shown) is provided in a surface of the electrode 502/the instrument branch body. Alternatively or in addition, a single light tunnel 520 of this type can serve for both excitation and reception of reflected light—with the appropriate filters. This means that a filter, which corresponds to the remission wavelength range, is placed after the light source, but the remaining light is directed into the tissue and received by the same and/or an adjacent opening, and returned to the sensor via the same reflective plane 524.

FIG. 14 shows the light guidance in the area of the instrument branch 501 according to the sixth embodiment in the light tunnel 520. The incoming light coming from the light source is fed into the light tunnel 520 and is deflected at the angled mirroring plane 524 at a predetermined angle (preferably with an angle between 0° and 90°). The light is radiated into the tissue through the mirror(s)/mirroring surface(s)/mirroring plane(s) 524, and the remitted light is directed/guided to a sensor by another light tunnel (not shown) having the same structure.

FIG. 15 shows an area of an instrument branch 601 according to a seventh embodiment. The instrument branch 601 has an electrode 602 which is received by an instrument branch body 608. The electrode 602 has a first electrode surface 604 and a second electrode surface 606 on the surface of the instrument branch body 608 which is provided and adapted to come into contact with the tissue. Light sources 610 and sensors 612 (not shown in detail) are integrated into the instrument branch body 608. The instrument branch body 608 comprises light exit openings 614 through which the light from a light source 610 is directed and radiates into/enters the tissue from the tissue contact surface. Furthermore, the instrument branch body 608 comprises light entrance openings 616 (not shown more in detail) through which the light radiates/enters from the tissue into/through the tissue contact surface of the instrument branch body 608 into a light tunnel 620 which terminates in a sensor. Light from the light source to the light exit opening 614 is also directed through a second light tunnel (not shown). At least one partially translucent plane 626 is introduced into the light tunnel 620, which transmits a portion of an electromagnetic radiation, hence is translucent for a portion of the light, and reflects a portion of the light. Preferably, the partially translucent plane is a partially translucent mirror, and more preferably, a plurality of partially translucent planes 626 are arranged in series in the light tunnel.

FIG. 16 shows the light guidance in the area of the instrument branch 601 according to the seventh embodiment in a light tunnel 620. The incoming light coming from the light source is fed into the light tunnel 620. The incoming light coming from the light source is fed into the light tunnel 620 in a straight line/in a directional manner/in a parallelly directed manner. By guiding by means of at least one partially translucent mirror 626 in the light tunnel 620, the light is guided/reflected/mirrored over angled regions/angles or the like. The light passing through a partially translucent mirror 626 is incident on another partially translucent mirror 626, which is arranged at the same angle as that of the previous mirror, and so on. Through the partially translucent mirror/mirroring surface/mirroring plane 626, the light is radiated into the tissue and the remitted light is directed/guided to a sensor by another light tunnel (not shown) having the same structure.

FIG. 17 shows an area of an instrument branch 701 according to an eighth embodiment. The instrument branch 701 comprises an electrode 702. The electrode 702 is located on an instrument branch body 708 of the instrument branch 701. In the instrument branch 701, for example, in an actuating portion or grip portion of the instrument branch 701, light sources 710 and sensors 712 are provided remotely from the instrument branch body 708, preferably externally (not shown in detail). The instrument branch body 708 comprises at least one light tunnel 720 through which light of the light source is directed and from which light radiates into/enters the tissue. The instrument branch body 708 comprises at least one other light tunnel 720 through which the light from the tissue is directed to a sensor. In this embodiment, the light tunnels 720 are formed by optical waveguides, such as, for example, optical fibers.

FIG. 18 shows the light guidance in the area of the instrument branch according to the eighth embodiment in a light tunnel 720. The incoming light coming from the light source is totally reflected at the inner surface of the light tunnel 720, and can thus be guided through the light tunnel 720. Due to the total reflection at the inner side of the light tunnel 720, the light can also be guided through bent areas/at least a bend or the like.

FIG. 19 shows an area of an instrument branch 801 according to a ninth embodiment. The instrument branch 801 comprises an electrode 802. The electrode 802 has a first electrode surface 804 and a second electrode surface 806 on the tissue contact surface of its instrument branch body, which is provided and adapted to come into contact with the tissue. Light sources 810 and sensors 812 are incorporated into the instrument branch body 808 (not shown in detail). The instrument branch body 808 also comprises light exit openings 814 through which the light from a light source is guided and radiates into/enters the tissue. The instrument branch body also includes light entrance openings 816 through which the light from the tissue in/through the instrument branch body radiates into/enters a light tunnel 820 which terminates in a sensor. Light from the light source to the light exit opening 814 is directed through the same light tunnel. In other words, light exit openings 814 can act as light entrance openings 816 and vice versa. At least two partially translucent planes 626 are introduced into the light tunnel 820, which transmit a portion of an electromagnetic radiation, hence, are translucent for a portion of the light, and reflect a portion of the light. Preferably, the partially translucent plane is a partially translucent mirror, and more preferably, a plurality of partially translucent planes 626 are arranged in series in the light tunnel. Due to this arrangement in this embodiment, a partially translucent mirror each is assigned to each of a light exit opening 814 or a light entrance opening 816.

FIG. 20 shows the light guidance in the area of the instrument branch 801 according to the ninth embodiment in a light tunnel 820. The incoming light coming from the light source is fed into the light tunnel 820. The incoming light coming from the light source is fed into the light tunnel 820 in a straight line/in a directional manner/in a parallelly directed manner. By guiding by means of at least two partially translucent mirrors 826 in the light tunnel 820, the light is guided/reflected/mirrored over angled areas/angles or the like. The light passing through a partially translucent mirror 826 is incident on at least one other partially translucent mirror 826, which is arranged at the same angle as the previous mirror, and so on. Through the partially translucent mirror/mirroring surface/mirroring plane 826, the light is irradiated into the tissue and the remitted light is directed/guided from the same light tunnel 820 but through an adjacent opening to a sensor. In yet other words, an opening is both a light exit opening and a light entrance opening for an adjacent opening.

FIG. 21 shows an area of an instrument branch 901 according to a tenth embodiment. The instrument branch 901 comprises an electrode 902, wherein in this embodiment, the instrument branch body and the electrode correspond to the previous embodiments in terms of their structure and arrangement. Accordingly, in the instrument branch 901, for example, in an actuating portion or grip portion of the instrument branch 901, light sources 910 and sensors 912 are provided remotely from the tissue contact surface of the instrument branch body (not shown in detail). The instrument branch body 908 includes light exit openings 914 through which the light from a light source is directed and from which light radiates into/enters the tissue. The instrument branch body further includes light entrance openings 916 through which the light from the tissue radiates/exits into a light tunnel 920 which terminates in a sensor. The light from the light source to the light exit opening 914 is directed through at least one light tunnel 920. The light from the light entrance opening 916 to the sensor is directed through at least one other light tunnel 920 (of the same design). Thus, in this embodiment, at least two light tunnels 920 are formed in the instrument branch body 908. The light exit opening(s) 914 and light entrance opening(s) 916 are alternately provided in the instrument branch body. At least one mirrored/reflective oblique/angled plane 924 is formed in the light tunnel 920.

FIG. 22 shows the light guidance in the area of the instrument branch 901 according to the tenth embodiment in the light tunnel 920. The incoming light coming from the light source is fed into the light tunnel 920, and deflected at the angled mirroring plane 924 at a predetermined angle (preferably with an angle between 0 and 90°). Through the mirror/mirroring surface/mirroring plane 924, the light is irradiated into the tissue, and the remitted light is directed/guided to a sensor by another light tunnel 920 having the same structure.

FIG. 23 shows a bipolar instrument branch according to the above embodiments. The embodiments one through ten are provided and adapted to be used in a bipolar medical HF instrument, wherein two instrument branch bodies are preferably pivotally mounted relative to each other, and define a tissue receiving gap between each other.

FIG. 24 shows opposing detectors and illuminations on a bipolar HF instrument. In this case, the light exit openings 1014 of the illuminations and the light entrance openings 1016 of the detectors are respectively located on opposing instrument branches/instrument branch bodies.

FIG. 25 shows a schematic diagram of a medical device 1100 according to the invention. A light source 1110 is provided and adapted to emit light. A sensor 1112 is provided and adapted to detect light. The light source emits the light through a light exit opening 1114. The sensor 1112 receives the light through a light entrance opening 1116. The light sources 1110 and the sensors 1112 are in communication with data lines 1130 and 1132 which are located in a channel 1118. The channel 1118 to is formed in an instrument branch body 1128 which also receives the electrodes in an insulating manner. The one instrument branch body, in which the electrode 1134 is received, clamps the tissue 1138 with an instrument branch body in which the opposite electrode 1136 is received. The electrode 1134 and the electrode 1136 are in communication with the lines 1140 and 1142. The data lines 1130 and 1132 as well as the lines 1140 and 1142 are in communication with a calculating unit 1144 which comprises a storage medium 1146.

FIG. 26 shows an example of a medical high frequency surgical instrument 1000 according to the invention, comprising a first instrument branch 1001 and a second instrument branch 1002. An instrument branch body 1008 is formed at the distal end of the first instrument branch 1001, and an actuating portion or grip portion 1009 is formed at the proximal end of the first instrument branch 1001.

The invention claimed is:

1. A medical high frequency surgical instrument comprising:
   at least one instrument branch,
   at least one light source which generates a first light with a certain illumination light spectrum which can be emitted in a direction towards a tissue, and
   at least one sensor, which is provided and adapted to measure a remission spectrum of a second light which is reflected by the tissue as a result of light impingement by the at least one light source, and to convert the measured remission spectrum into a detector signal according to the measured remission spectrum,
   wherein a calculating unit is provided and adapted to:
   receive the detector signal from the at least one sensor,
   calculate a theoretical remission spectrum based on a solution for describing a light propagation in the tissue, assuming estimated volume fractions of individual tissue components which are present in the tissue,
   adapt the theoretical remission spectrum to the measured remission spectrum;
   calculate at least one volume fraction of a first tissue component from the measured remission spectrum via a minimization algorithm with which the theoretically calculated remission spectrum is fitted to the measured remission spectrum by varying respective volume fractions of the individual tissue components present in the tissue;
   calculate at least an absorption maximum from an absorption spectrum of the tissue;
   calculate a temperature in the tissue by comparing the absorption maximum with at least one reference; and
   control or adjust or switch off the medical high frequency surgical instrument based on the calculated at least one volume fraction of the first tissue component and one or both of:
   the calculated temperature, and
   a calculated tissue impedance of the tissue component.

2. The medical high frequency surgical instrument according to claim 1, wherein the at least one reference is stored in the calculating unit in the form of a predetermined absorption maximum at a certain temperature.

3. The medical high frequency surgical instrument according to claim 1, which is moreover provided, adapted and configured to apply at least one light source and the at least one sensor to the tissue.

4. The medical high frequency surgical instrument according to claim 1, wherein the medical high frequency surgical instrument is provided, adapted and configured to control, adjust, or switch off, when the calculated temperature reaches a predetermined temperature.

5. The medical high frequency surgical instrument according to claim 1, wherein the medical high frequency surgical instrument is provided, adapted and configured to control, adjust, or switch off the medical high frequency surgical instrument online.

6. The medical high frequency surgical instrument according to claim 1, wherein the medical high frequency surgical instrument is provided, adapted and configured in order to perform a tissue identification during a sealing process.

7. The medical high frequency surgical instrument according to claim 1, wherein the at least one light source and the at least one sensor are spaced apart from each other.

8. The medical high frequency surgical instrument according to claim 1, wherein the instrument branch forms an instrument branch body, which forms one half of an operable instrument jaw of the medical high frequency surgical instrument, and comprises at least one electrode, which is provided and adapted to come into contact with the tissue, and is arranged in or on the instrument branch body, wherein the at least one light source and the at least one sensor are arranged in or on the instrument branch body.

9. The medical high frequency surgical instrument according to claim 1, wherein the instrument branch forms an instrument branch body, which forms one half of an operable instrument jaw of the medical high frequency surgical instrument, and comprises at least one electrode, which is provided and adapted to come into contact with the tissue, and is arranged in or on the instrument branch body, wherein at least one light tunnel is arranged in or on the instrument branch, through which the first light from the at least one light source is directed to and/or the second light is directed from the tissue.

10. A tissue identification method for controlling a medical high frequency surgical instrument with at least one instrument branch, the method comprising the steps of:
   generating a first light with an illumination spectrum which can be emitted in a direction towards a tissue by means of at least one light source;
   measuring a remission spectrum of a second light, which is obtained by remission of the first light from the tissue by at least one sensor;
   converting the measured remission spectrum with the at least one sensor into a detector signal;
   sending the detector signal to a calculating unit;
   calculating a theoretical remission spectrum based on a solution for describing a light propagation in the tissue using the calculating unit, assuming estimated volume fractions of individual tissue components which are present in the tissue;

calculating at least one absorption maximum from an absorption spectrum of the measured remission spectrum with the calculating unit;

calculating a temperature in the tissue by comparing the absorption maximum with at least one reference using the calculating unit;

calculating at least one volume fraction of a first tissue component by varying respective volume fractions of the individual tissue components, which are present in the tissue, via a minimization algorithm with which the calculated theoretical remission spectrum is fitted or adapted to the measured remission spectrum using the calculating unit; and controlling or adjusting or switching off the medical high frequency surgical instrument with the calculating unit based on the calculated at least one volume fraction of a tissue component and one or both of:

the calculated temperature, and a calculated tissue impedance of the tissue component.

11. A machine readable storage medium comprising the control steps according to claim 10.

* * * * *